(12) United States Patent
Nurminen et al.

(10) Patent No.: US 7,196,238 B2
(45) Date of Patent: Mar. 27, 2007

(54) PROCESS FOR DIMERIZING LIGHT OLEFINS

(75) Inventors: Matti Nurminen, Porvoo (FI); Antti Pyhälahti, Helsinki (FI); Pirjo Siira, Järvenpää (FI); Marja Tiitta, Porvoo (FI)

(73) Assignee: Fortum OYJ, Espoo (FI)

( * ) Notice: Subject to any disclaimer, the term of this patent is extended or adjusted under 35 U.S.C. 154(b) by 0 days.

(21) Appl. No.: 10/383,763

(22) Filed: Mar. 10, 2003

(65) Prior Publication Data

US 2004/0181106 A1    Sep. 16, 2004

(51) Int. Cl.
*C07C 2/02*    (2006.01)

(52) U.S. Cl. ............... 585/517; 510/518; 510/327; 510/324

(58) Field of Classification Search ........... 585/517, 585/510, 518, 327, 324
See application file for complete search history.

(56) References Cited

U.S. PATENT DOCUMENTS

| | | | |
|---|---|---|---|
| 4,777,316 A * | 10/1988 | Harandi et al. ........... | 585/517 |
| 6,008,426 A | 12/1999 | Van Oorschot et al. | |
| 6,111,159 A * | 8/2000 | Huff et al. ............... | 585/529 |
| 6,518,473 B2 * | 2/2003 | Miller et al. ............ | 585/517 |
| 2003/0100811 A1 | 5/2003 | Dakka et al. | |

FOREIGN PATENT DOCUMENTS

| EP | 0 994 088 B1 | 4/2000 |
|---|---|---|
| EP | 1 242 342 B1 | 9/2002 |
| WO | WO 00/23402 | 4/2000 |
| WO | WO 01/46095 | 6/2001 |

* cited by examiner

*Primary Examiner*—Tam M. Nguyen
(74) *Attorney, Agent, or Firm*—Birch, Stewart, Kolasch & Birch, LLP.

(57) ABSTRACT

The invention relates to a process for dimerizing lower, olefinic hydrocarbons. In particular, the present invention concerns a process for dimerizing $C_3$-, $C_4$ and $C_5$-olefins with a medium pore zeolite under process conditions allowing selective dimerization According to the invention, fresh olefinic hydrocarbon feedstock is fed to a reaction system including at least one reaction zone and at least one separation zone. The olefinic hydrocarbon feedstock is contacted with an acid catalyst at conditions in which at least a part of the olefins dimerizes. The effluent from the reaction zone is conducted to the separation zone where dimerized reaction product is separated from said effluent.

37 Claims, 2 Drawing Sheets

PROCESS FOR DIMERIZING LIGHT OLEFINS

BACKGROUND OF THE INVENTION

1. Field of the Invention

The present invention relates to the selective production of $C_6$–$C_{10}$ hydrocarbons useful as automotive fuel components. In particular, the present invention concerns a process for dimerizing lower, olefinic hydrocarbons in the presence of a zeolite catalyst under process conditions allowing selective dimerization.

2. Description of Related Art

Light olefin dimers are useful intermediates in the manufacture of different products, like alcohols, ketones and carboxylic acids. Highly branched trimethylolefins and trimethylparaffins are useful as gasoline octane number enhancers.

Zeolites represent a diverse family of crystalline microporous materials with a wide variety of topologies, chemical compositions and acid-base properties. It is commonly known that zeolites are commercially used as catalysts in several different hydrocarbon transformation reactions, such as cracking and isomerization.

Many processes for utilization of light olefins for the production of high quality transportation fuels are known. The Mobil Olefin to Gasoline and Distillate (MOGD) process converts propylene and butylene to olefinic distillate in high yields. The MOG or Mobil Olefins to Gasoline process is an extension of the MOGD. In MOG, the reaction conditions allow aromatics formation. Oligomerization of isobutene from $C_4$ olefins over zeolite catalysts has been disclosed in several U.S. patents.

An essential feature of selective dimerization of light olefins is to prevent oligomerization, which is the successive reaction of dimerization. Selective dimerization of isobutene over trimerization and higher oligomerization is known from U.S. Pat. No. 3,325,465, DE Patent No. 3 542 171 and International Patent Application WO 01/46095. In U.S. Pat. No. 3,325,465, the use of nickel and cobalt ions in 13× zeolite is disclosed. In DE Patent No. 3 542 171, the selective dimerization of isobutene into trimethylpentene is made with bismuth or lead doped zeolite. In WO 01/46095, large pore zeolite Beta has been found to be selective for isobutene dimerization to the trimethylpentene in the presence of oxygenates. In addition, the reference teaches that dimerization can be carried out in the presence of an alcohol.

There are a few commercial dimerization processes. Institut Francais du Petrole (IFP) has developed a process for dimerization of light olefins (Dimersol). The Octol process, developed by UOP and Huls AG, produces linear octenes, which are the raw-materials of plastics softeners. Homogeneous catalysts are used in the processes.

There are several processes based on ion exchange resins available, as described e.g. in U.S. Pat. Nos. 4,375,576 and 4,100,220. They have many good properties but they all have the drawback of being totally dependant on oxygenate moderator, which improves the selectivity. This moderator has to be recycled and there is usually the same amount of oxygen containing side products present in the dimerized product. When the reason to use dimerization is elimination of oxygenates from the components, these are highly undesired. Moreover, the oxygenates make hydrogenation of dimerized product more difficult.

All problems connected to oxygenates are self-evidently solved if they can be removed from the process altogether.

As the above review of the art shows, none of the known solutions provides dimerization at high selectivity in combination with facile separation of unreacted components. There is a need for a process that operates with heterogeneous catalysts at industrially operable conditions without polar compounds.

SUMMARY OF THE INVENTION

It is an objective of the present invention to eliminate the problems of prior art and provide a novel process for dimerizing olefinic feedstocks.

The invention is based on the idea of dimerizing $C_3$- to $C_5$-olefins in liquid phase in a reaction sequence comprising at least one reaction zone and at least one separation zone. The reaction is carried out at conditions in which at least a part of the olefins dimerize. The separation zone is arranged after the reaction zone, and a circulation flow is circulated from the separation zone back to the dimerization. The process is carried out essentially in the absence of polar compounds.

According to the invention, the olefinic feedstock comprising $C_3$–$C_5$ isoolefins is contacted with a medium pore zeolite in order to dimerize the isoolefins into $C_6$–$C_{10}$ dimers.

The conditions of process are selected so as to favour selective dimerization of isoolefins. A dimer selectivity of more than 85% can be obtained when dimerization is carried out in the presence of a heterogeneous zeolite catalyst. The catalyst can be any zeolite that is active in dimerization reactions. Such zeolites are exemplified by natural and synthetic medium pore size zeolites, such as ZSM-5, ferrierite, ZSM-22 and ZSM-23. These and similar catalysts having a pore size in the range of about 2 to 8 Å (0.2–0.8 nm), preferably 4 to 6 Å (0.4–0.6 nm), are active and selective for trimethyl olefins.

More specifically, the process according to the present invention is mainly characterized by what is stated in the characterizing part of claim 1.

The invention also provides the use of a synthetic or natural medium pore zeolite as an acid catalyst for dimerization of an olefinic feed containing unsaturated hydrocarbons, selected from the group consisting of isobutene, 1-butene, 2-butene, linear $C_5$-olefins and branched $C_5$-olefins.

Considerable advantages are achieved by means of the present invention. In conventional processes, selective dimerization over oligomerization is a desired but not easily achieved goal. When using the process of the present invention, a high selectivity of dimers can be achieved thus making the production more efficient compared with previously used processes.

According to a preferred embodiment of the invention, the catalyst that permits a high conversion of monomers to dimers. The catalyst also gives a high selectivity of dimers. The conditions in the reaction zone can be optimized to match different production objectives. The process according to the present invention is suitable for dimerizing $C_3$-olefins to $C_5$-olefins or mixtures thereof.

With conventional techniques, regeneration of the catalyst often poses a threat to continuous operation of the process. In the present invention, the catalyst can be regenerated continuously, during process operation. The easy regeneration gives a possibility to handle feeds containing nitrogen and sulphur impurities, which is a considerable advantage compared to previous processes.

In prior art, it is common to operate dimerization processes in the presence of oxygenates or other polar compounds. Oxygenates and other polar compounds typically include water, ether or alcohol. Alcohols commonly used in dimerization processes include $C_1$–$C_5$ alcohols, e.g. methanol, ethanol, isopropanol or t-butanol. The alcohol may be primary, secondary or tertiary alcohol. Further examples include tert-amyl methyl ether, 2-butanol and 2-pentanol. According to the present invention, no oxygenates or polar compounds are required. This is a considerable advantage, because the separation of oxygenates from the dimerized product often poses problems in process design and operation. The design of process equipment can be simplified with no need for separation of oxygenates from the product flow. This means a simplified and more easily controlled process operation and savings in process equipment investments.

DETAILED DESCRIPTION OF THE INVENTION

Definitions

A "reaction zone" comprises at least one, typically two or three, reactor(s). The reactor can be any continuous type reactor, in which a solid catalyst can be placed and that is capable of handling liquid reagents. Advantageously, the reactor is a simple tubular reactor, a packed bed reactor or a fluidized bed reactor. The reactor can be a tubular reactor with multiple pipes, wherein the pipes are filled with catalyst. Other possibilities include a reactive distillation unit with side reactors. The operating pressure of the reactors depends on the type of the reactor and on the composition of the feed, typically it is desired to keep the reaction mixture in liquid phase. In order to be able to regenerate the catalyst during reactor operation, it is often advantageous to use at least two reactors that can be regenerated in turn. Another advantageous mode of operation is to use a reactor, in which the catalyst can be regenerated continuously.

For the purposes of the present invention, "separation zone" designates a separation system that according to an embodiment comprises a distillation system comprising one or more distillation columns. The feed plate can be selected for each column to be most advantageous in view of the overall process. The distillation column can be any column suitable for distillation, such as a packed column, or one provided with valve, sieve or bubble-cap trays.

"Isooctene" and "di-isobutene" are both products of isobutene dimerization. Thus they can be used interchangeably to designate 2,4,4-trimethyl-1-pentene and 2,4,4-trimethyl-2-pentene or a mixture thereof.

"Isooctane" and "di-isobutane" comprise the corresponding hydrogenated paraffinic compounds.

"Effluent" contains the desired product of the dimerization reaction in the reaction zone. When only $C_3$-olefins, only $C_4$-olefins or only $C_5$-olefins are fed to the process, it is clear that the resulting product of the mutual reactions of the olefins yield dimers. However, when $C_3$-, $C_4$- and $C_5$-olefins are present in the feed, in addition to dimerization, also reactions between the different olefins may occur. The word "dimer" is also used for the reaction products in the specification for reasons of simplicity, but it is to be understood that when different lower olefins are present in the feed, the reaction mixture typically contains also some amount of the $C_9$-olefins.

The Overall Process

According to a first preferred embodiment of the invention, the hydrocarbon feed containing isobutene or linear butenes or a mixture thereof, is contacted with an acid catalyst together in a essentially oxygenate-free reaction system comprising at least one reaction zone and at least one separation zone. The conditions in said reaction zone are essentially oxygenate-free, which means that the amount of polar compounds is less than 0.5 mole-% of the olefinic hydrocarbons fed into the reaction zone. The conditions are such that at least a part of the isobutene is dimerized to isooctene. The flow from said reaction zone is introduced into a separation zone, where the main part of the dimerized reaction product is separated from the unreacted product. Advantageously, at least a part from the unreacted product is circulated from the separation zone back to the dimerization.

The feed of the process according to the present invention is a hydrocarbon mixture containing olefins. The feed comprises olefins to be dimerized at least 10 wt-%, preferably at least approximately 20 wt-%. As already described, the olefins are selected from the group of propene, linear 1- or 2-butene, isobutene and linear or branched $C_5$-olefins. Alternatively, the feed can comprise a mixture of any or every of the olefins listed above. Typically, the feed comprises dimerizable components; either $C_4$-olefins, preferably isobutene, whereby isooctene is produced, or $C_5$-olefins, whereby substituted $C_{10}$-olefins are produced. It is clear that both $C_4$- and $C_5$-olefins can be present in the feed, whereby a great variety of products is produced. The composition of the product flow is discussed later.

According to the first preferred embodiment, in which $C_4$-hydrocarbons are dimerized, the hydrocarbon mixture in the feed comprises at least 10 wt-%, preferably at least approximately 15 wt-% isobutene. The feed can consist of pure isobutene, but in practice, the feedstock readily available comprises $C_4$-based hydrocarbon fractions from oil refining. Preferably, the feed comprises a fraction obtained from isobutane dehydrogenation, when the feed comprises mainly isobutene and isobutane and possibly small amounts of $C_3$- and $C_5$-hydrocarbons. Typically the feed then comprises 40–60 wt-% of isobutene and 60–40 wt-% isobutane, usually there is 5–20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert $C_4$-hydrocarbons and approximately 5 wt-% of $C_3$–, $C_5$- and heavier hydrocarbons altogether.

Due to the high isobutene content in the flow from the isobutane dehydrogenation the amounts of inert hydrocarbons in the recycling flows remain relatively small. The dehydrogenation fraction is very suitable for producing a product with a very high content of the dimerized isobutene.

The feed for producing isooctene is also possible to select from the group containing $C_4$-fractions of FCC, TCC, DCC and RCC or from the $C_4$-fraction after the removal of butadiene, also called Raffinate 1 of an ethylene unit. Of these FCC, RCC, TCC and Raffinate 1 are preferred, since the hydrocarbon fractions can be used as such, possibly after removing the heavier ($C_{8+}$) fractions. Raffinate 1 is typically composed of approximately 50 wt-% isobutene, approximately 25 wt-% linear butenes and approximately 25 wt-% paraffins. The product from the FCC is typically composed of 10–50, in particular 10–30 wt-% isobutene, 20–70 wt-% 1- and 2-butene and approximately 5–40 wt-% butane. As an example of a typical FCC-mixture, the following can be presented: approximately 17 wt-% isobutene, approximately 17 wt-% 1-butene, approximately 33 wt-% 2-butene and approximately 33 wt-% butane, and others.

Also isobutene prepared from chemicals can be used as feed.

According to another preferred embodiment of the invention, the olefins present in the olefinic feedstock are selected from the group of linear and branched $C_5$-olefins, such as linear pentene, 2-methyl-1-butene, 2-methyl-2-butene, 3-methyl-1-butene, and mixtures thereof.

According to an embodiment of the invention, the feedstock comprises aromatic hydrocarbons, paraffins and mixtures of these.

If the present invention is used for converting linear butenes, the linear butenes are preferably selectively isomerized to 2-butene as completely as possible. In this case, it is preferable to add a separate side reactor circulation to the process configuration. The temperature in this reactor is preferably higher than in the prereactor or circulation reactor in order to increase the conversion of dimerization.

FCC and corresponding hydrocarbon flows are suitable to use, e.g., in cases where the conventional MTBE unit is used to produce a product mixture comprising isooctene and MTBE.

According to the second preferred embodiment of the invention, in which $C_5$-olefins are dimerized, the feed comprises olefins selected from the group of linear and branched $C_5$-olefins, or a mixture thereof. Thus, the olefins typically present in the feed comprise linear pentene, 2-methyl-1-butene, 2-methyl-2-butene, 3-methyl-1-butene. Also some amounts of $C_6$-olefins, typically at least 5 wt-% can be present in the feed.

Typically, the feed in the second preferred embodiment is FCC gasoline, light FCC gasoline, pyrolysis-$C_5$-gasoline, TCC gasoline, RCC gasoline and Coker gasoline, typically the $C_5$-fraction of FCC gasoline, and can thus comprise also some $C_6$-olefins. Advantageously, the FCC fraction is fractionated to obtain as pure $C_5$-olefin fraction as possible where other $C_5$-hydrocarbons are present in less than 15 wt-%, preferably less than 5 wt-%. It is possible to use a fraction comprising also $C_6$-olefins. Typically, the feed then comprises 20 to 60 wt-%, in particular 30 to 50 wt-% $C_5$-olefins, 10 to 30 wt-%, in particular 15 to 25 wt-% $C_6$-olefins and 15 wt-% or less paraffinic hydrocarbons pentanes.

According to the third preferred embodiment, the feed comprises both $C_4$- and $C_5$-olefins. In this case, the feed is typically selected from the group comprising FCC, TCC, DCC and RCC or from the $C_4$-fraction after the removal of butadiene, also called Raffinate 1 of an ethylene unit, FCC gasoline, light FCC gasoline, pyrolysis-$C_5$-gasoline, TCC gasoline, RCC gasoline and Coker gasoline. A fraction readily available comprises $C_4$ and $C_5$ fractions from FCC. Advantageously, a fraction comprising at least 10 wt-%, preferably at least 15 wt-% $C_4$-olefins and at least 10 wt-%, preferably at least 15 wt-% $C_5$-olefins is used. Typically the amounts of $C_4$-olefins and $C_5$-olefins are approximately equal, although a slight dominance of $C_4$-olefins in the fraction is also usual.

According to the invention, the hydrocarbon feed containing olefins is contacted with an acid catalyst selected from the group of natural and synthetic medium pore zeolites together in a reaction zone at conditions in which at least a part of the olefins is dimerized. In case where the olefin feed comprises $C_3$- to $C_5$-olefins, also reactions between different olefins occur, thus forming higher (meaning up to $C_{10}$)-olefins. The effluent from the reaction zone is introduced into a separation zone, where the main part of the dimerized reaction product is separated to form a first product containing unreacted hydrocarbons and a second product containing the dimerized olefins.

According to the first preferred embodiment, $C_4$-olefins are dimerized. The compositions of the feed have already been discussed, and product compositions then are as follows:

When mainly dimers of isobutene are produced, they are typically present in the product flow in at least 85 wt-%, preferably at least 90 wt-%. Other components typically present in the product flow are trimers of isobutene, 15 wt-% or less, preferably 10 wt-% or less, tetramers of isobutene in less than 0.2 wt-% and other hydrocarbons in less than 1 wt-% preferably less than 0.1 wt-%.

Regardless of the aimed product composition most (65–100 wt-%, typically 85–100 wt-%, preferably 95–100 wt-%) of the dimers produced by the process are 2,4,4-trimethyl pentenes. When the product stream is hydrogenated, a mixture comprising isooctane is obtained. The fraction of other trimethyl pentanes (e.g. 2,3,4-trimethyl pentane) as well as the fraction of dimethyl hexanes in the mixture remains extremely small. Thus the octane number (RON) of the fuel component is high, typically at least 95, preferably approximately 98–100.

According to the second preferred embodiment, dimers of $C_5$-olefins are produced. The product is typically as follows:

At least 65 wt-%, preferably at least 70 wt-%, $C_5$-dimers, 5–32 wt-%, preferably 5–29 wt-% olefin trimers, less than 1 wt-%, preferably less than 0.5 wt-% olefin tetramers. Because no oxygenate is fed to the process, the amount of oxygenates in the process and in the final product is very small. When the composition is hydrogenated, a composition useful as a fuel component is obtained.

According to the third embodiment, dimers of both $C_4$- and $C_5$-olefins are produced. In addition also $C_4$- and $C_5$-olefins react and form $C_9$-olefins. The product composition then comprises at least 65 wt-%, preferably at least 70 wt-%, $C_5$-dimers, $C_4$-dimers and $C_9$-olefins, 5–32 wt-%, preferably 5–28.5 wt-% olefin trimers, less than 1 wt-%, preferably less than 0.5 wt-% olefin tetramers. When the composition is hydrogenated, a composition useful as a fuel component is obtained.

Regardless of the aimed product composition most (50–100 wt-%, typically 60–100 wt-%, preferably 90–100 wt-%) of the dimers and $C_9$-olefins produced by the process are isooctene, tetramethylpentenes and trimethylhexenes. When the product stream is hydrogenated, a mixture comprising corresponding hydrogenated hydrocarbons is obtained. The relative abundance of individual components varies depending on the ratio of the reactive $C_4$- and $C_5$-components in the feed. When the product stream is hydrogenated, a mixture comprising isooctane, tetramethylpentanes and trimethylhexanes is obtained. Thus the octane number (RON) of the fuel component is high, typically at least 95, preferably approximately 98–100.

The dimer fraction of the reaction product for a feed comprising (among other, less reactive compounds) both $C_4$- and $C_5$-isoolefins (in a ratio 45:55) includes trimethylpentenes 20–30 wt-%, in particular 25–28 wt-%, tetramethylpentenes and trimethylhexenes 20–30 wt-%, in particular 20–25 wt-%, tetramethylhexenes 4–8 wt-%, in particular 5–6 wt-%, and trimethylheptenes 2–5 wt-%, in particular 3–4 wt-%. The rest of the dimer product is less branched olefins.

The product has a vapour pressure of 10–20 kPa and a distillation point (90 vol-%, ASTM D86) is equal or less than 180° C.

A part of the first reaction product is circulated from the separation zone back to the reaction zone. It is to be understood that although the following description refers to a sideflow in the singular tense, which is the typical configuration, it is also possible to withdraw two or more sideflows and circulate all those flows back to dimerization.

According to an advantageous embodiment, the reaction zone comprises two reactors in parallel. The feed comprising fresh olefinic feed and recycled first product may be fed to one of the reactors, and the second reactor can be recovered simultaneously. The effluent from the reaction zone is introduced into a separation zone, where the main part of the dimerized reaction product is separated to form a first product containing unreacted hydrocarbons and a second product containing the dimerized olefins.

The flow of the recycled first product is 20–150 wt-%, preferably 30–130 wt-%, in particular 40–120 wt-% of the flow of the fresh feed.

The selectivity of the dimerization reaction in a process according to our invention is high. According to an embodiment, the selectivity of dimerized olefins, expressed as the ratio of the molar amount of dimeric compounds to the total molar amount of converted olefins, is in excess of 0.8, in particular in excess of 0.9.

According to the invention, an acid catalyst is used. In these conditions, medium pore zeolites, like ZSM-5, ferrierite, ZSM-22 and ZSM-23, are active and selective for trimethylolefins. The following table describes the properties of some advantageous catalysts that can be used in this invention.

TABLE 1

Zeolite materials selective in the olefin dimerization in our invention.

| Zeolite | ZSM-5 | ZSM-23 | ZSM-22 | Ferrierite |
|---|---|---|---|---|
| Pore system | 3-dimensional | 1-dimensional | 1-dimensional | 2-dimensional |
| Pore size | 5.1 Å × 5.5 Å and 5.3 Å × 5.6 Å | 4.5 × 5.2 Å | 4.6 Å × 5.7 Å | 4.2 Å × 5.4 Å and 3.5 Å × 4.8 Å |

As will become apparent from Table 1, the zeolite catalyst to be used in the present invention have pore sizes in the range of about 2 to 8 Å, preferably about 3 to 6 Å (0.3 to 0.6 nm).

In this invention, the zeolite is selected from the group consisting of synthetic and natural zeolites containing about 0.1 to 5 wt-%, preferably about 0.3 to 3 wt-%, in particular about 0.5 to 2 wt-%, aluminium. The zeolite is selected from the group consisting of ZSM-5, ZSM-22, ZSM-23, ferrierite and ion-exchanged zeolites prepared therefrom. Such ion-exchanged zeolites may contain counter-ions selected from the group of alkali metal and alkaline earth metal ions, such as sodium, potassium, calcium and magnesium.

Zeolite catalysts used according to the invention can be prepared by any suitable method known in the art. A common method to prepare zeolites is preparation by hydrothermal synthesis. In hydrothermal synthesis, a reaction mixture containing a source of silicon oxide, a source of aluminium oxide and if necessary an organic template together with an alkali metal source are stirred together at appropriate temperature. The formed crystals are separated from the mixture, and calcinated in air at such temperatures and such a time that the organic template is removed. The ions of the calcinated material are exchanged to ammonium ions. The material is subjected to suitable conditions to decompose ammonium ions in order to form ammonia and protons.

The composition of zeolite material can differ in chemical composition depending on the original composition of preparation method and treatment performed after preparation.

Both removal of the organic template and the ammonia present form acid sites in the zeolite catalyst. These acid sites are active in dimerization.

According to another preferred embodiment of the invention, acid sites in the zeolites are formed by ion exchange with protons in a liquid Brönsted acidic medium. The catalyst exhibits Brönsted acid sites.

According to an embodiment of the invention, acid sites are formed through hydrolysis of hydration water by polyvalent cations.

The composition of zeolite material can be differ in chemical composition depending on the original composition of preparation method and treatment performed after preparations. Zeolite catalyst can be treated with any treatments known in prior art. Common treatments are vapor treatments and acid and silicon tetrachloride treatments for dealumination, ion exchange treatments for modification of pore size and acidity, impregnations and gas phase treatments for introducing metals on the surface of zeolites.

Zeolite catalysts in use comprise a zeolite and a carrier. The carrier can be any carrier of prior art. Suitable carriers are for example silica, alumina, clay or any mixture of these. The catalyst can have 10–100% zeolite, the rest of the catalyst is the carrier. The carrier serves to give formability, hardness and in some cases additional, suitable activity to the dimerization reaction.

In the process according to the invention, the dimerization is carried out in the liquid phase. In liquid phase, the separation of unreacted components is relatively easy.

According to an advantageous embodiment, the reactor is a reactive distillation unit with side reactors.

The catalyst of our invention can be regenerated. This makes it possible to work in a continuous process with two reactors in that the one is in a reaction stage and the other is in the regeneration stage. This gives the opportunity to handle a feed with a high level of nitrogen and sulphur impurities that deactivates the catalysts.

The temperature of the reaction zone is typically 50–200° C., preferably 80–150° C. The upper level of the temperature range is set by avoiding unwanted side reactions.

The effluent from the reaction zone is conducted to a separation zone, where components are separated from one another. The composition of the product flow depends on the process parameters and on the composition of the feed. As already discussed, the process of the present invention can be used for producing dimerized product from olefinic feedstock. The olefins present in the feed can be either $C_3$-olefins, $C_4$-olefins, $C_5$-olefins or a mixture of these. Thus it is clear that the composition of the product flow depends essentially on the fraction used as the feedstock.

According to the first preferred embodiment, $C_4$-olefins are dimerized. The compositions of the feed have already been discussed, and product compositions then are as follows:

The dimer fraction of the reaction product for a feed comprising (among other, less reactive compounds) both $C_4$- and $C_5$-isoolefins (in a ratio 45:55) includes trimethylpentenes 20–30 wt-%, in particular 25–28 wt-%, tetramethylpentenes and trimethylhexenes 20–30 wt-%, in particular 20–25 wt-%, tetramethylhexenes 4–8 wt-%, in particular 5–6 wt-%, and trimethylheptenes 2–5 wt-%, in particular 3–4 wt-%. The rest of the dimer product is less branched olefins.

According to an embodiment, a part of the first product, which is not recycled, is transferred to alkylation.

According to an embodiment, the second product is subjected to hydrogenation to provide a partly or totally hydrogenated product.

Preferred process configurations are presented in the following.

Figure 1:
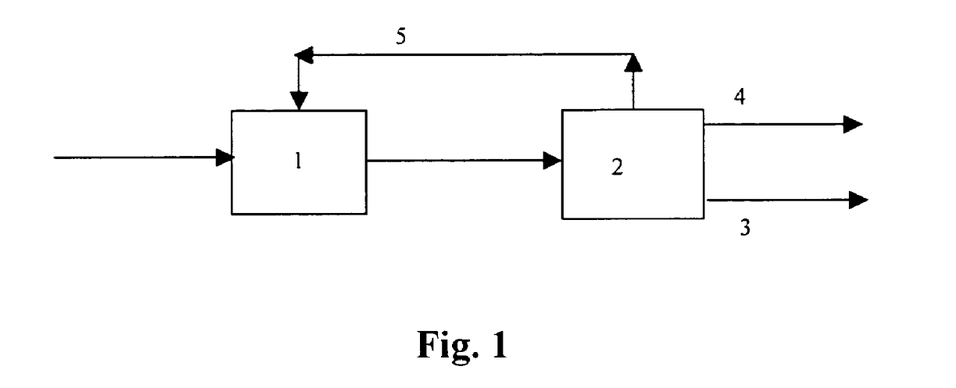
FIG. 1 depicts in a schematic fashion the process configuration of the basic technical solution of the invention.

According to a preferred embodiment of the invention, the process comprises a reaction zone 1 and a separation zone 2, as presented in FIG. 1. The product is formed in the reaction zone and in the separation zone the product is separated from unreacted components in flow 3. The inert components and the remaining feed leave the process in flow 4. The remaining feed is returned to the process along with flow 5. The numerals refer to the numerals in FIG. 1.

The reaction zone comprises one or several reactors. Many reactors of a continuous type capable of housing a solid catalyst and a liquid reagent are suitable for the invention. According to an embodiment of the invention, the reactor must allow regeneration of the catalyst. The regeneration can be done during continuous process operation. Alternatively, two or several reactors can be used in parallel, this allows regenerating one reactor when other is being operated.

A typical dimerization system consists of one or more reaction sections followed by product separation and arrangements for recycling of the unreacted reactants. Several reaction and product separation stages may be connected in series if conversion requirement is high.

According to an embodiment of the invention, the reaction zone comprises any reactor type suitable for liquid phase operation and in which a solid catalyst can be used. These reactor types include a fixed bed reactor, a moving bed reactor, a mixing tank reactor, a fluidized bed reactor, or a spouted bed reactor or a combination of these reactors.

In order to meet the requirements for continuous operation, the dimerization catalyst must be regenerated regularly. It is often necessary to include facilities for catalyst regenaration in the reactor system. If continuous operation is not imperative, it is of course possible to pause process operation for catalyst regeneration. However, in industrial operation it is preferred to have several reactors that can be regenerated one at a time, while the others are in production. A example of such arrangement according to our invention is two or more fixed bed reactors connected in such a manner that each of them can be separated from the process for changing or regenerating the catalyst.

Another preferred option in dimerization operations is to use a reactor from which the catalyst can be extracted continuously for regeneration. In an embodiment of our invention, a fluidized bed or spouted bed reactor is used, from which the catalyst can be extracted continuously and recycled through a regeneration facility.

According to a preferred embodiment of the invention, the separation zone comprises a distillation column. The product flow from the reaction zone comprises light hydrocarbons remaining from the hydrocarbon feed, and oligomers formed in the reactor having a boiling point substantially higher than that of the feed. This makes separation by distillation simple.

According to an embodiment of our invention, the separation zone is preferably a distillation zone. The reactants are monomers and the product is a mixture of oligomers and thus they have significantly different boiling points making separation by distillation easy. Considering the ease of separation, a flash drum, evaporator, stripper, or fractionator and other distillation devices known in the art can be used.

Figure 2:
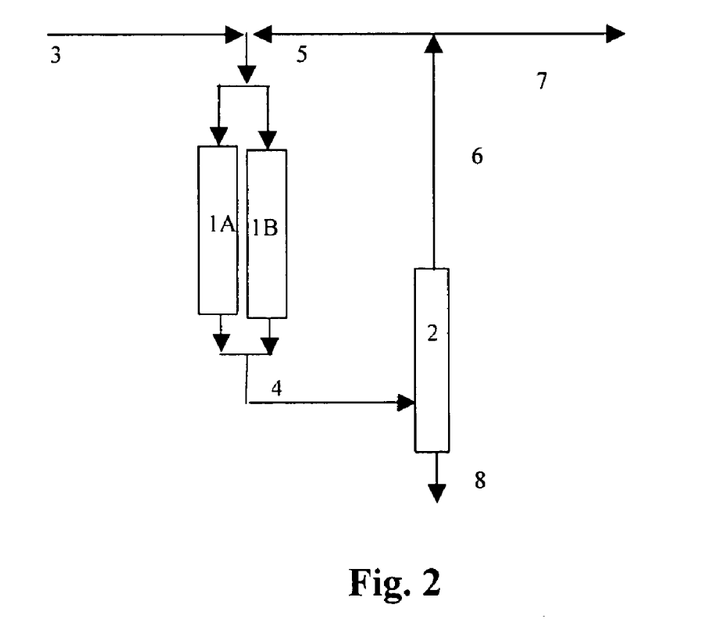
FIG. 2 depicts an embodiment in which the reaction zone comprises two reactors in parallel

Another preferred embodiment of the invention is presented in FIG. 2. The reaction zone comprises two reactors in parallel 1A and 1B used in turn. This means that when one reactor is being regenerated, the other reactor is used for the dimerization. The separation zone comprises a distillation column 2. Flow 8 comprises the product flow leaving from the separation zone. The flow 6 at the top of the distillation column comprises the unreacted feed. A part of the feed 7 is withdrawn from the process and the other part is directed back to the separation zone in order to raise the yield of the reaction zone.

Figure 3:
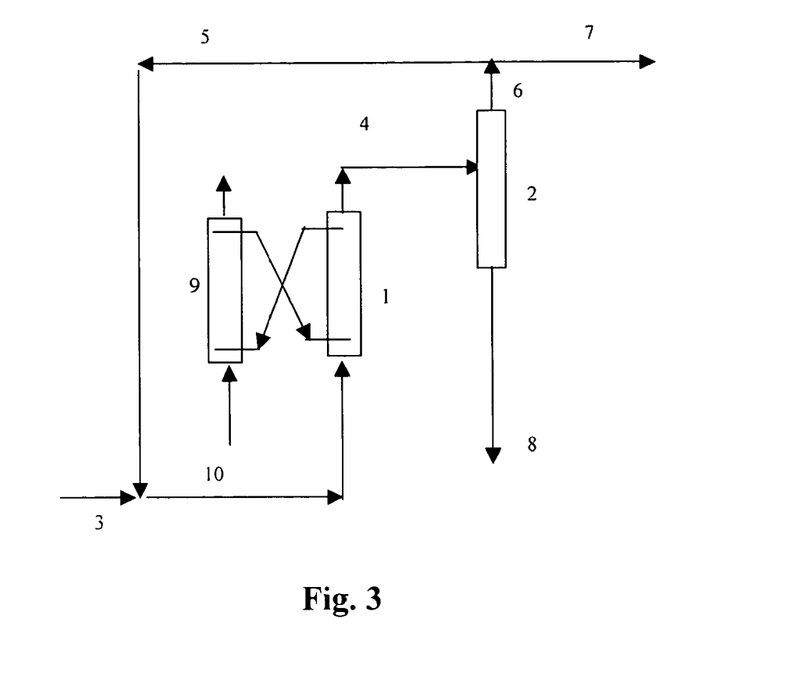
FIG. 3 depicts an embodiment in which the reaction zone comprises a fluidized bed reactor with continuous catalyst regeneration

Another advantageous embodiment of our invention is presented in FIG. 3. In this embodiment, the reactor is a fluidized bed reactor and the catalyst is continuously regenerated in a regenerator unit 9.

Figure 4:
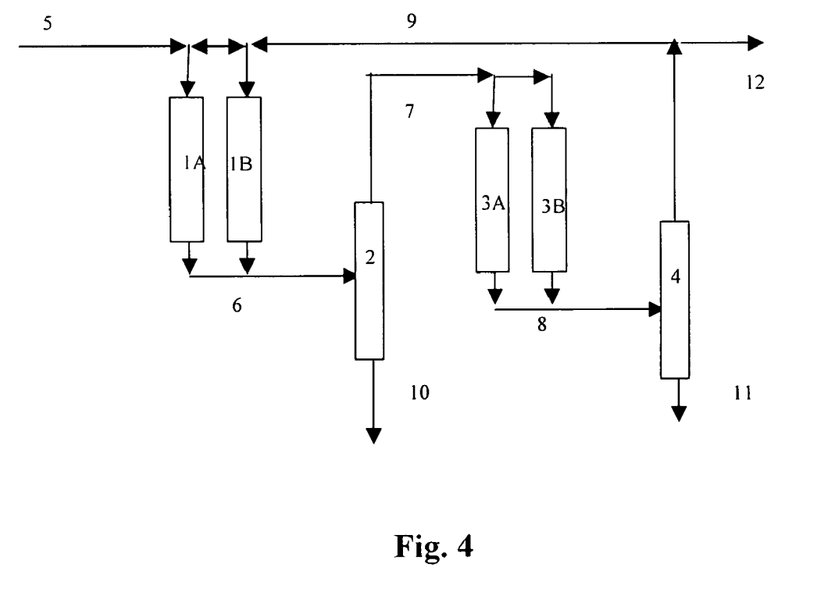
FIG. 4 depicts an embodiment in which the reaction zone comprises 2 reaction zones and 2 separation zones.

FIG. 4 presents another preferred embodiment of the invention. The yield of the reaction zone is improved by connecting two reaction zones. Both reaction zones comprise two reactors in parallel, i.e. 1A/1B and 3A/3B. In the first separation zone 2, the dimer formed in the first reaction zone is separated in flow 10 from the unreacted components in flow 7, and in the second separation zone 4 the dimer formed in the second reaction zone is separated in flow 11 from the unreacted components in flow 12. Some of the unreacted components are returned to the feed in flow 5 via flow 9.

EXAMPLES

Seven examples are presented in order to further illustrate the invention.

Example 1

Comparative example with commercial ion exchange resin catalyst. The present invention does not include the catalyst.

Isobutene is dimerized continuously in a reactor tube at temperature 80° C. and at pressure 20 bar. The catalyst used in reaction was a commercial ion exchange resin used in the commercial dimerization process. The catalyst load was 9.4 g dry catalyst. Before loading into the reactor tube the catalyst was rinsed with deionized water and dried in oven 110° C. for 16 hours.

The feed contained 30 wt-% isobutene and 70 wt-% isobutane, but no polar components. The flow rate of the feed was 100 g/h.

Table 2 presents the results of the example 1. The results showed that conversion of isobutene was very high but the selectivity to dimers was poor.

TABLE 2

Summary of the results for example 1

| | |
|---|---|
| Conversion of isobutene, % | 99.8 |
| Selectivity to dimers, % | 12.7 |
| 2,4,4-trimethylpentenes, wt-% | 3.1 |
| C8-olefins, wt-% | 4.3 |
| C8+, wt-% | 29.4 |

Example 2

Comparative example with commercial solid phoshoric acid catalyst used in the commercial dimerization process. The water in feed is required for activation of catalyst.

TABLE 3

The test conditions for example 2

| | Examples | | |
|---|---|---|---|
| | 2a | 2b | 2c |
| WHSV, Total (g feed/g catalyst * h) | 3.4 | 7 | 5.7 |
| WHSV, Isobutene (g isobutene/g catalyst * h) | 0.7 | 1.4 | 1.2 |
| Feed | 20 wt-% isobutene, 31 wt-% n-butane, 48 wt-% iso-octane | | |
| Water content of feed, ppm | 100 | | |
| Temperature, ° C. | 138 | 140 | 140 |
| Pressure, bar | 21 | 21 | 31 |

TABLE 4

Summary of the conversion and selectivities for example 2

| | Example 2a | Example 2b | Example 2c |
|---|---|---|---|
| Conversion of isobutene, % | 97–98 | 96–98 | 98 |
| Selectivity to dimers, % | 77–79 | 80–85 | 84–86 |

Example 3

Comparative Examples with Zeolite Catalyst

The catalyst was ZSM-5 zeolite in proton form. Its Si/Al-ratio was 24, BET-surface area 550 m$^2$/g, crystallinity 80% and particle size less than 0.001 mm. The feed had 39% isobutene.

The conditions for comparative examples are presented in Table 5.

TABLE 5

The experimental conditions of comparative examples with zeolite catalyst.

| | Example 3a | Example 3b | Example 3c |
|---|---|---|---|
| Temperature, ° C. | 150 | 100 | 100 |
| Pressure, bar | 10 | 10 | 10 |
| WHSV, 1/h | 4 | 4 | 20 |

TABLE 6

Summary of the conversion and selectivities for example 3

| | Example 3a | Example 3b | Example 3c |
|---|---|---|---|
| Conversion of isobutene, % | 97–98 | 98–100 | 16–70 |
| Selectivity to dimers, % | 40–48 | 20–35 | 45–77 |

Example 4

Example Describing the Present Invention

The catalyst is same to example 3. The reaction were made at temperature 100° C., in pressure 20 bar and with WHSV 20. The pressure was sufficient to keep the reaction mixture in liquid phase. The selectivities to dimers were above 80%.

TABLE 7

Summary of the conversion and selectivities for example 4

| Conversion, % | Selectivity to dimers, % |
|---|---|
| 67.9 | 85.9 |
| 59.9 | 88.0 |
| 46.8 | 91.4 |
| 41.6 | 92.6 |
| 34.0 | 93.7 |
| 28.6 | 94.5 |
| 24.1 | 95.2 |
| 21.6 | 95.4 |
| 19.8 | 95.4 |
| 16.1 | 95.6 |
| 13.8 | 95.9 |

Example 5

Example Describing the Present Invention

The catalyst is same to example 4. The catalyst was reactivated with purging in inert atmosphere. The reaction were made at temperature 100° C., in pressure 20 bar and with WHSV 20. The pressure was sufficient to keep the reaction mixture in the liquid phase. The selectivities were above 80%.

TABLE 8

Summary of the conversion and selectivities for example 5

| Conversion, % | Selectivity to dimers, % |
|---|---|
| 80.4 | 81.4 |
| 77.3 | 83.4 |
| 61.1 | 88.6 |
| 54.7 | 90.1 |
| 46.4 | 91.8 |
| 42.0 | 92.6 |
| 35.4 | 93.7 |
| 32.8 | 94.1 |
| 26.8 | 94.8 |
| 24.1 | 95.0 |
| 19.5 | 95.4 |
| 17.1 | 95.9 |

Example 6

Example Describing the Present Invention

The catalyst was ZSM-22 zeolite. Its Si/Al-ratio was 58, BET-surface area 210 m²/g, crystallinity 70% and particle size less than 0.001 mm. The feed had 39% isobutene.

The reaction were made at temperature 100° C., in pressure 20 bar and with WHSV 20. The pressure was sufficient to keep the reaction mixture in the liquid phase. The selectivities were above 80%.

TABLE 9

Summary of the conversion and selectivities for example 5.

| Conversion, % | Selectivity to dimers, % |
|---|---|
| 68.2 | 80.4 |
| 54.5 | 80.4 |
| 37.8 | 90.4 |
| 29.8 | 92.0 |
| 23.0 | 93.0 |
| 18.4 | 93.6 |
| 14.9 | 93.9 |
| 12.0 | 94.7 |
| 10.0 | 94.2 |
| 8.2 | 94.9 |
| 7.2 | 94.3 |
| 6.4 | 94.7 |

Example 7

Example Describing the Present Invention

The catalyst is same to example 6. The catalyst was reactivated with purging in inert atmosphere. The reaction were made at temperature 100° C., in pressure 20 bar and with WHSV 20. The pressure was sufficient to keep the reaction mixture in the liquid phase. The selectivities were above 80%.

TABLE 10

Summary of the conversion and selectivities for example 7

| Conversion, % | Selectivity to dimers, % |
|---|---|
| 50.6 | 87.0 |
| 40.0 | 89.4 |
| 32.2 | 90.6 |
| 25.8 | 91.7 |
| 21.4 | 92.4 |
| 17.9 | 92.8 |
| 15.0 | 93.0 |
| 12.7 | 93.4 |
| 11.6 | 93.6 |
| 9.7 | 93.7 |
| 8.3 | 94.8 |
| 6.9 | 94.2 |

Example 8

Example Describing the Present Invention

The catalyst was a zeolite with ferrierite structure. Its Si/Al-ratio was 29, BET-surface area 330 m²/g, crystallinity 80% and particle size less than 0.001 mm. The catalyst was reactivated with purging in inert atmosphere. The reaction were made at temperature 100° C., in pressure 20 bar and with WHSV 20. The pressure was sufficient to keep the reaction mixture in the liquid phase. The feed had 39% isobutene. The selectivities were above 80%.

TABLE 11

Summary of the conversion and selectivities for example 8.

| Conversion, % | Selectivity to dimers, % |
|---|---|
| 77.8 | 82.1 |
| 70.3 | 84.7 |

The invention claimed is:

1. A process for dimerizing olefinic, lower hydrocarbons, comprising:
feeding a fresh olefinic hydrocarbon feedstock to a reaction zone;
contacting the olefinic hydrocarbons of the feedstock in liquid phase with an acid catalyst in the reaction zone, wherein the acid catalyst is selected from the group of natural and synthetic medium pore zeolites;
withdrawing an effluent containing dimerized olefins from the reaction zone;
conducting the effluent to a separation zone, wherein the dimerized reaction product is separated from said effluent;
withdrawing from said separation zone a first product containing unreacted hydrocarbons;
recycling at least a part of the first product to the reaction zone; and
recovering from said separation zone a second product containing dimerized olefins;
wherein the conversion rate of the olefinic hydrocarbons fed to the reaction zone is adjusted so as to provide a ratio of dimeric compounds to the total molar amount of converted olefins of at least 0.8.

2. The process according to claim 1, wherein the temperature of the reaction zone is maintained at 50 to 200° C.

3. The process according to claim 1 or 2, wherein the pressure of the reaction zone is maintained above the vapour pressure of the mixture present in the reactors.

4. The process according to claim 1, wherein the pressure of the reaction zone is maintained at 10 to 50 bar.

5. The process according to claim 1, wherein the part of the first product, which is not recycled, is transferred to alkylation.

6. The process according to claim 1, wherein the zeolite is selected from the group consisting of synthetic and natural zeolites containing about 0.1 to 5 wt-% of aluminum.

7. The process according to claim 6, wherein the zeolite is selected from the group consisting of ZSM-5, ZSM-22, ZSM-23, ferrierite and ion-exchanged zeolites prepared therefrom.

8. The process according to claim 6, wherein the catalyst exhibits Brönsted acid sites.

9. The process according to claim 1, wherein the olefins present in the olefinic feedstock are selected from the group of isobutene, 1-butene, 2-butene, linear and branched C₅-olefins.

10. The process according to claim 9, wherein the feedstock comprises 10 to 100 wt-% of isobutene.

11. The process according to claim 1, wherein the olefins present in the olefinic feedstock are selected from the group of linear and branched C₅-olefins.

12. The process according to claim 1, comprising combining the recycled first product with the fresh feed to form a combined feed of olefins for the reaction zone.

13. The process according to claim 1, wherein the flow of the recycled first product is 20–150 wt.

14. The process according to claim 1, wherein the dimerization reaction is carried out at a selectivity of dimerized olefins, expressed as the ratio of the molar amount of dimeric compounds to the total molar amount of converted olefins, is more than 0.8.

15. The process according to claim 1, wherein the dimerization reaction is carried essentially in the absence of polar compounds.

16. The process according to claim 15, wherein the amount of polar compounds is less than 0.5 mole-% of the olefinic hydrocarbons fed into the reaction zone.

17. The process according to claim 15, wherein the olefins are dimerized without any additional feed of polar compounds.

18. The process according to claim 15, wherein the dimeric product contains a maximum concentration of polar compounds corresponding to the concentration of those compounds in the olefinic feed.

19. The process according to claim 15, wherein oxygenates are removed from the olefinic feed.

20. The process according to claim 1, wherein the second product is partly or totally hydrogenated.

21. The process according to claim 1, wherein the separation zone comprises a distillation zone.

22. The process according to claim 21, wherein the first product comprises the distillate of the distillation zone and wherein the second product comprises the bottoms product of the distillation zone.

23. The process according to claim 21 or 22, wherein the distillation zone is operated so as to provide a product having vapour pressure of 10–20 kPa and a distillation point (90 vol-%, ASTM D86) is equal or less than 180° C.

24. The process according to claim 1, wherein the dimerization process is carried out in a reactive distillation system including at least one reaction zone and at least one distillation zone, said at least one reaction zone including at least one reactor and said at least one distillation zone including at least one distillation column.

25. The process according to claim 1, wherein isooctene is produced from a feed comprising isobutene, and the isooctene is optionally hydrogenated to yield isooctane.

26. A process for dimerizing olefinic, lower hydrocarbons, comprising:
feeding an olefinic hydrocarbon feedstock to a reaction zone, wherein the olefinic hydrocarbon feedstock contains unsaturated hydrocarbons, selected from the group consisting of isobutene, 1-butene, 2-butene, linear $C_5$-olefins and branched $C_5$-olefins;
contacting said olefinic hydrocarbon feedstock in liquid phase with an acid catalyst in the reaction zone, wherein the acid catalyst is selected from the group of natural and synthetic medium pore zeolites; and
recovering from said reaction zone a product containing dimerized olefins;
wherein the conversion rate of the olefinic hydrocarbons fed to the reaction zone is adjusted so as to provide a ratio of dimeric compounds to the total molar amount of converted olefins of at least 0.8.

27. The process according to claim 1, wherein the step of contacting said olefinic hydrocarbons of the feedstock with an acid catalyst is conducted substantially in the absence of oxygenates and polar compounds.

28. The process according to claim 26, wherein the step of contacting said olefinic hydrocarbons of the feedstock with an acid catalyst is conducted substantially in the absence of oxygenates and polar compounds.

29. A process for dimerizing olefinic, lower hydrocarbons, comprising:
feeding a fresh hydrocarbon feedstock comprising tertiary olefins, branched hydrocarbons and/or branched olefins to a reaction zone;
contacting the olefinic hydrocarbons of the feedstock in liquid phase with an acid catalyst in the reaction zone, wherein the acid catalyst is selected from the group of natural and synthetic medium pore zeolites;
withdrawing an effluent containing dimerized olefins from the reaction zone;
conducting the effluent to a separation zone, wherein the dimerized reaction product is separated from said effluent;
withdrawing from said separation zone a first product containing unreacted hydrocarbons;
recycling at least a part of the first product to the reaction zone; and
recovering from said separation zone a second product containing the dimerized olefins;
wherein the conversion rate of the olefinic hydrocarbons fed to the reaction zone is adjusted so as to provide a ratio of dimeric compounds to the total molar amount of converted olefins of at least 0.8.

30. The process of claim 2, in which the temperature is from 80 to 150° C.

31. The process of claim 4, in which the pressure is from 15 to 25 bar.

32. The process of claim 6, in which the zeolite contains from 0.3 to 3 wt-% aluminum.

33. The process of claim 6, in which the zeolite contains from 0.5 to 2 wt-% aluminum.

34. The process of claim 10, in which the feedstock comprises 15–50 wt-% of isobutene.

35. The process of claim 13, in which the flow of the recycled first product is 30–130 wt-% of the of the flow of the fresh feed.

36. The process of claim 13, in which the flow of the recycled first product is 40–120 wt-% of the flow of the fresh feed.

37. The process of claim 14, in which the total molar amount of converted olefins is more than 0.9.

* * * * *